(12) United States Patent
Will et al.

(10) Patent No.: US 8,091,435 B2
(45) Date of Patent: Jan. 10, 2012

(54) ULTRASONIC MEASURING ARRANGEMENT

(75) Inventors: Thomas Will, Vogtsburg (DE); Martin Deutscher, Freiburg (DE)

(73) Assignee: MIB GmbH Messtechnik und Industrieberatung, Ihringen (DE)

( * ) Notice: Subject to any disclaimer, the term of this patent is extended or adjusted under 35 U.S.C. 154(b) by 0 days.

(21) Appl. No.: 12/909,155

(22) Filed: Oct. 21, 2010

(65) Prior Publication Data

US 2011/0088483 A1   Apr. 21, 2011

Related U.S. Application Data

(63) Continuation of application No. PCT/EP2009/001245, filed on Feb. 20, 2009.

(30) Foreign Application Priority Data

Apr. 21, 2008  (DE) .......................... 10 2008 019 992

(51) Int. Cl.
*G01F 1/66* (2006.01)
(52) U.S. Cl. .................................................. 73/861.28
(58) Field of Classification Search ... 73/861.26–861.28
See application file for complete search history.

(56) References Cited

U.S. PATENT DOCUMENTS

| 4,545,244 A * | 10/1985 | Yasuda et al. .................. 73/195 |
| 5,716,038 A | 2/1998 | Scarffe |
| 5,905,207 A * | 5/1999 | Schalk ........................ 73/861.28 |
| 6,418,796 B1 * | 7/2002 | Baumoel .................... 73/861.28 |
| 7,360,450 B2 * | 4/2008 | Muller ........................ 73/861.28 |

FOREIGN PATENT DOCUMENTS

| DE | 3911408 | 10/1990 |
| DE | 3941546 | 6/1991 |
| DE | 4330363 | 3/1995 |
| DE | 10109161 | 9/2002 |
| DE | 10120355 | 10/2002 |
| EP | 0088235 | 2/1983 |
| EP | 0457999 | 12/1990 |
| EP | 0681162 | 4/1995 |
| EP | 1413858 | 4/2004 |
| EP | 1760436 | 3/2007 |
| WO | 9420822 | 9/1994 |
| WO | 2007065557 | 6/2007 |

* cited by examiner

*Primary Examiner* — Jewel V Thompson
(74) *Attorney, Agent, or Firm* — Volpe and Koenig, P.C.

(57) ABSTRACT

An ultrasonic measuring arrangement (1) for the flow, speed of sound, density, viscosity and/or temperature measurement of flowing media, including a measurement tube (2) having a measurement section (3), with the tube being disposed in an area of a measurement housing (4). At least two ultrasound transmitting receivers are spaced apart as sensors for sound transmission through the measurement section (3) in the direction of flow of a medium, and opposite thereto, and for signal recording. In order to provide an ultrasonic measuring arrangement (1) that is simple and inexpensive to produce, has a small nominal diameter and permits direct sound transmission through the measurement section (3) at as low a transmission output as possible, the measurement tube (3) is configured together with the measurement housing (4) as a one-piece housing part (5) free of seals and seams, and the sound path form an acute angle with the flow direction of the medium.

10 Claims, 2 Drawing Sheets

ULTRASONIC MEASURING ARRANGEMENT

CROSS-REFERENCE TO RELATED APPLICATIONS

This application is a continuation of PCT/EP2009/001245, filed Feb. 20, 2009, which claims the benefit of German Patent Application No. 10 2008 019 992.3, filed Apr. 21, 2008, both of which are incorporated herein by reference as if fully set forth.

BACKGROUND

The invention relates to an ultrasonic measuring arrangement for the flow, speed of sound, density, viscosity, and/or temperature measurement of flowing media, comprising a measurement tube having a measurement section, said tube being disposed in an area of the measurement housing, wherein the ultrasonic measuring arrangement comprises at least two ultrasound transceivers disposed at a distance as sensors for sound transmission through the measurement section in the direction of flow of a medium and opposite thereto, and for signal recording. Additionally the invention relates to a method for producing such an ultrasonic measuring arrangement.

In order to establish a measuring section for good sound transmission during the use of ultrasonic measuring arrangements, particularly in the field of flow rate measurements of flowing media, various concepts are known to embody measurement sections inside housings. For small nominal diameters in the range of up to approximately 25 mm, from EP 0 088 235 and EP 0 681 162 a U-shape is known, and alternatively a Z-form or a double-Z form are also known, and depending on the space available and the application additional, basically arbitrary, complicated forms of measurement sections can be used.

All measurement sections known exhibit the disadvantage that, for reasons of production technology, their profile required for the measurement process requires a multi-part component and the respective parts must subsequently be connected by way of welding creating seams or seals. This circumstance in turn is disadvantageous in that the respective seals may become leaky and develop capillaries between the housing and the seal. On the other hand, welding spots may show pores, inclusions, or other irregularities. The transported medium to be measured can adhere to these weak spots, which particularly in the food industry can lead to problems with regards to hygiene. Here, another problem can occur in the chemical industry, if residual media remains, which e.g., may endanger the personnel during disassembly of the device.

Within the above-mentioned small nominal diameters there are other systems known, for example, from DE 101 20 355, DE 39 11 408, DE 39 41 546, and WO 2007/065557, which operate by way of reflection or even multiple reflections. However, each reflection removes a portion of the irradiated sound energy, so that here strong signal transmissions are required, which in turn may lead to problems with respect to electromagnetic tolerances, or the signal received weakens to such an extent that it becomes hard to distinguish it from the permanent background noise and thus the measurement collection requires additional expenses.

From DE 101 09 161 a measuring arrangement is known, in which inside a device having a large nominal diameter, a smaller diameter is quasi simulated by a nozzle in a measuring tube, by way of the nozzle concentrating the flow to a small area. However, such arrangements have a fixed, predetermined direction of flow and cannot measure any backflow.

Finally, U.S. Pat. No. 5,716,038 discloses a measuring arrangement having sensors that are contacted by the media, which arrangement is complicated in its production and potentially susceptible to sealing problems. EP-A-1 413 858 discloses a measuring arrangement, in which the measurement essentially occurs cross-wise in reference to the direction of flow. WO 94/20822 discloses a measuring arrangement, in which sensors must be subsequently introduced into recesses, provided for said purpose at the measurement tube, and which subsequently must be closed and sealed.

SUMMARY

Therefore the object is to provide an ultrasonic measuring arrangement, which can be produced in an easy and cost-effective manner, and which with small nominal diameters of measurement section avoids the disadvantages of subsequently assembled parts, and which allows direct sound transmission through the measurement section with reasonable transmission strength.

The object is attained in an ultrasonic measuring arrangement of the type mentioned at the outset, in which the measurement tube of the arrangement is embodied free from seals and seams and is embodied in one piece with a housing part of the measuring arrangement in a manner free from seals and seams, and the sensors are arranged in the end sections of the measurement tube such that the sound path forms an acute angle with the direction of flow of the medium that is not zero degrees. The respective measurement tube of the ultrasonic measuring arrangement according to the invention can therefore be produced particularly easily in a one-step injection molding process and consequently it is free from seals, seams, and thus also capillaries, particularly in its portions contacted by the medium.

A flawless measurement of flow rates with little errors is achieved in an embodiment of the ultrasonic measuring arrangement, in which the sound path is embodied free from reflections.

In order to protect the sensitive sensors of the ultrasonic measuring arrangement from the exposure to the sometimes aggressive media to be measured, in one embodiment of the ultrasonic measuring arrangement advantageously the sensors may be arranged in the end sections of the measurement tubes in a contactless-less fashion with regards to the medium.

In order to achieve a reduction of the problems of impact sound always observed during the measurement using ultrasound beneficially ultrasonic converters are used as sensors with their size being as small as possible. This is facilitated by a further development of the ultrasonic measuring arrangement according to the invention in which the cross-section of the sound path changes over the longitudinal extension, with the area the medium is flowing through essentially remaining the same. Here, the channel for liquids is flattened with the cross-sectional area remaining approximately the same.

An embodiment easily integrated in the transportation path of the medium to be measured may comprise that the ultrasonic measuring arrangement is provided with connectors, which are arranged symmetrically in reference to a reflector level in the center of the housing extending perpendicularly to the longitudinal extension of the housing part.

An embodiment of the ultrasonic measuring arrangement facilitating the integration of additional installations at the measurement section may be provided such that an installation chamber is provided at the housing part in particular comprising an access opening at the side facing away from the measurement tube.

The sensors of the ultrasonic measuring arrangement must be connected to at least one signal processing device for creating, collecting, processing, and/or forwarding the ultrasonic signals. A beneficial further development is particularly suitable for its arrangement, in which the housing part combined with another housing part forms a particularly closed structural chamber, in which the installation of a signal processing device can be provided. The installation of the signal processing device is also possible entirely inside another housing part, and thus separated from the first one. Furthermore, additional housing parts can be mounted to the first one. In another embodiment of the ultrasonic measuring arrangement, one or more signal processing devices can be installed in the first housing part, which for this purpose may be provided such that it can be opened and closed.

Such embodiments of the ultrasonic measuring arrangement are particularly preferred, which comply with the regulations concerning hygiene and safety for applications in the food and the chemical industry, and for this purpose the measurement tube as well as the measurement housing and/or its parts are made from plastic, particularly from a food-compatible and/or high-resistance plastic, for example from polyethylene (PE) or another polyolefin, or a suitable polymer fluorocarbon, such as perfluoroalkoxy (PFA).

In order to fix the ultrasonic measuring arrangement, for example at a tank or at a suitable point along the transportation path of the medium, beneficially fastening elements to mount it are provided at the housing part, for example housing projections comprising loops or threaded holes.

The above-mentioned object is also attained in a method for producing an ultrasonic measuring arrangement, particularly an ultrasonic measuring arrangement as described above, comprising at least the following processing steps:
  i. Providing a mold;
  ii. Inserting two positive forms into the mold, which contact each other at one of their areas such that they complement each other to form the volume of the measurement tube;
  iii. Producing in a one-step molding process, in which the complete measurement tube including the accepts arranged outside the measurement tube for installing the sensors as well as the connections of the arrangement is formed in a manner free from seals and seams, wherein another housing part is produced from said mold during the same molding process that is embodied in one piece with the measurement tube in a manner free from seals and seams;
  iv. Demolding the mold and removing the molded one-piece part (5).

In this method, in a single, particularly simple production process, an ultrasonic measuring arrangement is provided, comprising a reflection-free sound path and in which particularly the portion of the ultrasonic measuring arrangement contacted by the medium is free from capillaries and hollow spaces, with the small nominal diameter of the measurement section allowing a comparatively low transmission power of the ultrasonic transceiver and here allowing a direct sound transmission through the measurement section.

In an advantageous variant of the method the positive forms are embodied identically and contact each other at a side area over an essential portion of their longitudinal extension such that the measurement tube is already formed by their molding. This way, only one embodiment of a positive form must be designed and then produced in several copies, with furthermore, at the mold itself, only the section of the housing part not directly related to the measurement section remains to be considered during the shape forming.

In order to advantageously predetermine the form of the measurement section to be subjected to sound transmission, in a preferred variant of the method the positive forms are each formed by a spike-like slide feed, with its cross-section changing over the length increasingly projecting into the mold. It is particularly preferred for the cross-section of the two adjacent slide feeds to form an area with almost parallel extending side bands in the center of the measuring section and rounded edges, not showing any corners.

In a beneficial further development of the method, another housing part is produced from said mold during the same molding process, particularly another housing part provided for installation at the first housing part, which can accept devices necessary for example to create, collect, and process a signal. The installation chamber for additional devices for the ultrasonic measuring arrangement may also be formed by the first housing part, though.

Another variant of the method according to the invention may additionally provide that during the production of the housing part either the sensors are integrated therein by inserting them into the mold before the molding process or it is provided that the sensors are subsequently arranged at the housing part at accepts accessible from the outside, so that after the molding process either a complete measuring arrangement is provided or it remains to be completed by sensors subsequently to be selected.

BRIEF DESCRIPTION OF THE DRAWINGS

In the following, the invention is explained in greater detail using the exemplary embodiments of the drawing. Here, it shows in a partially schematic illustration

DETAILED DESCRIPTION OF THE PREFERRED EMBODIMENTS

Figure 1:
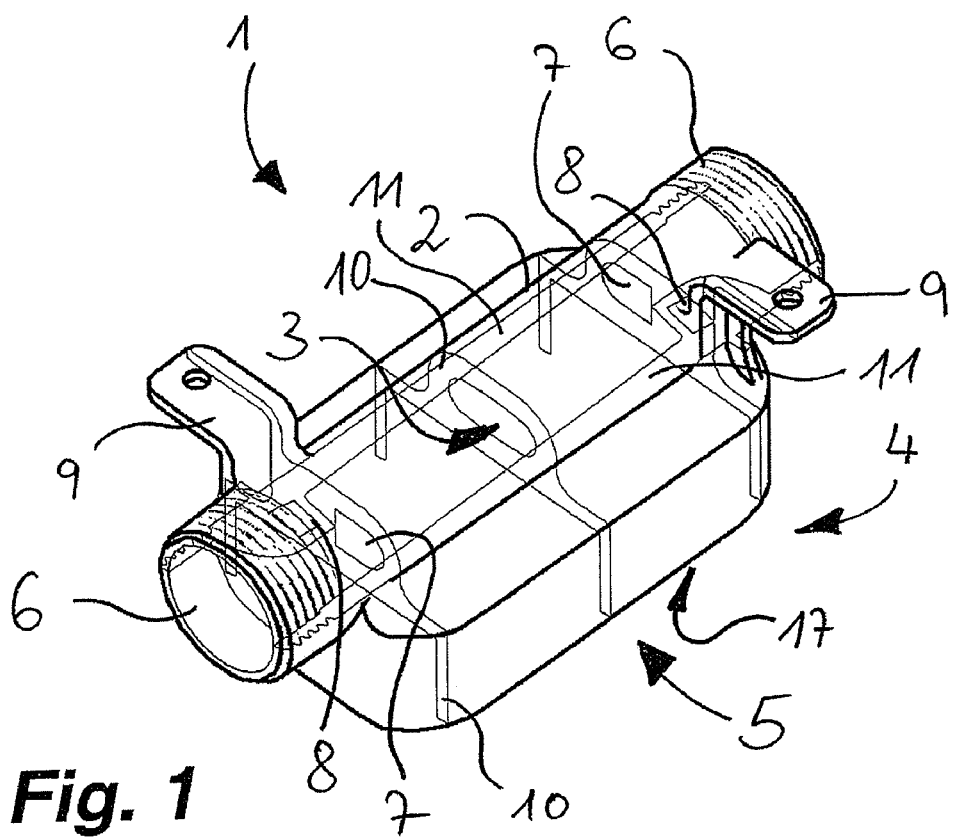
FIG. 1 is a perspective view of an ultrasonic measuring arrangement embodied in one piece with auxiliary cross-sections for visualizing longitudinal and perpendicular cross-sections along the sound path of the measurement section.

In FIG. 1, an ultrasonic measuring arrangement is discernible, in its entirety marked 1, for measuring the flow, speed of sound, density, viscosity, and/or temperature of flowing media. The measurement tube 2 of the ultrasonic measuring arrangement comprises a measurement section 3 and is arranged in a section of the measurement housing 4. The ultrasonic measuring arrangement 1 further comprises at least two ultrasound transceivers (not shown) as sensors, arranged spaced apart, for sound transmission through the measurement section 3 in the direction of flow of a medium and opposite thereto and to collect signals. The measurement tube 2 itself is here embodied in one piece without any seams or seals as well as having a measurement housing 4, free from seals and seems and being embodied as a one-piece part with the housing part 5 made from plastic in an injection-molding process, and the sound path forms with the direction of flow of the medium an acute angle, which is different from 0°.

The housing part 5 is provided with connections 6, which form the inlet and outlet of the medium to be transported and/or measured. These connections 6 are arranged symmetrical in reference to a reflector level, not shown, extending in the center of the housing perpendicularly to the longitudinal extension of the housing part 5. The two openings 7 of the measurement tube 2, located diagonally opposite each other, are provided at the ends of the connections 6 facing the measurement section 3. Next to the openings 7, respective recesses 8 for housing one sensor each are discernible, not contacted by the respective medium. The recesses 8 are arranged adjacent to the openings 7 of the measurement tube 2 such that a diagonal sound path is formed in the measurement path 3, free from reflections.

Figure 2:
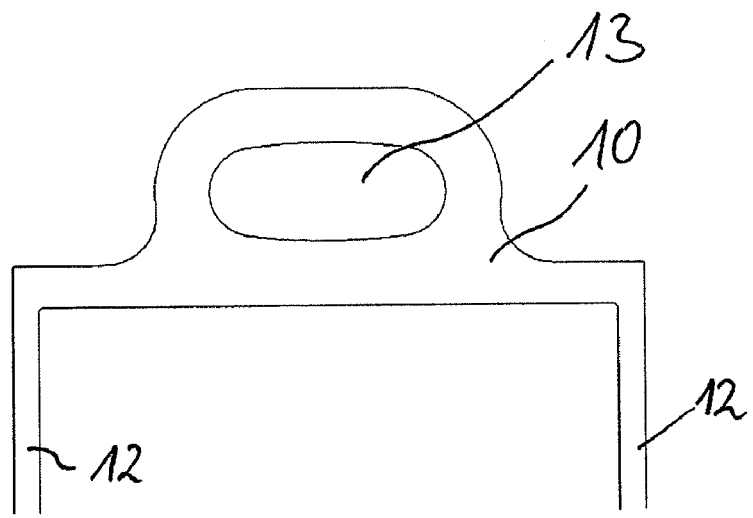
FIG. 2 is a level side view of an auxiliary cross-section of FIG. 1, taken from a central area of the measurement section.

The housing part 5 of the ultrasonic measuring arrangement 1 is shown with auxiliary cross-sections 10, 11, only serving visualization purposes, with the central one, positioned vertically, is also shown in FIG. 2. These auxiliary cross-sections 10, 11 represent a perpendicular and/or longitudinal cross-section of the housing part 5 at the location of their arrangement. Here, it is discernible that the housing part 5 is formed without any bottom at the side facing away from the viewer and comprises an installation chamber with an access opening 17. A bottom, for example embodied as a lid, not shown, may subsequently be arranged at the edge of the housing part 5, the lower one for the viewer, and said bottom may then be closed, for example after the installation of a signal processing device. Furthermore, combined the auxiliary cross-sections 10, 11 show the progression of the measurement section 3 inside the measurement tube 2 and allow the viewer to follow the sound path of the ultrasound between the sensors and to learn that the cross-section of the sound path changes over the longitudinal extension of the measurement section 3 while the area the medium flows through essentially remains the same.

Finally, it is discernible in FIG. 1 that at the upper side of the housing 5 facing the viewer two fixation elements 9 are arranged, located in the end sections of the housing part 5 and diagonally facing each other, which are embodied as projections with loops or threaded holes.

As already mentioned, FIG. 2 shows the level view of an auxiliary cross-section 10, as arranged in the central area of the housing part 5 in FIG. 1, which forms a cross-section through the plastic material of the housing part 5. Here, the brace-like edges 12 of the housing part 5 are discernible, which form a "U" open towards the bottom, as well as in the upper area it shows a hole-like opening encompassed by material of the housing part, which shows the cross-section of the measurement section 3 at this location. Here it is discernible that the cross-section of the measurement section is flattened compared to the one in the area of the opening 7 of the measurement section 3 without the cross-sectional area being considerably changed.

Figure 3:
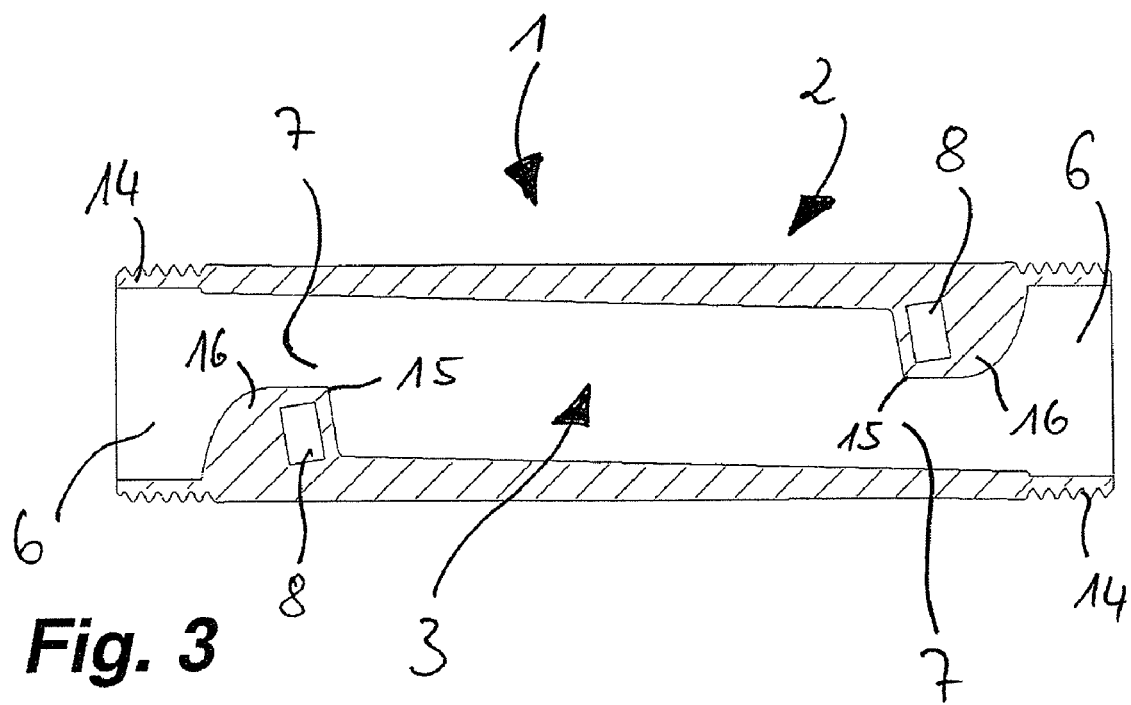
FIG. 3 is a side view of a longitudinal cross-section through the measurement tube of the ultrasonic measuring arrangement of FIG. 1.

FIG. 3 shows a longitudinal cross-section through the measurement section 3 of the ultrasonic measuring arrangement 1. Beginning at the connections 6, provided with exterior threads 14 to connect inlet and outlet lines, the measurement section 3 starts at openings 7 of the measurement tube 2, positioned diagonally across each other. Next to the openings 7, a respective recess 8 is discernible for installing a sensor, which is formed in a section 16 of the measurement tube 2 projecting from the edge. These sensors are then also positioned diagonally opposite each other such that a diagonal sound path is formed, particularly one free from reflections, and the sound path forms an acute angle with the longitudinal extension of the measurement tube 2, but also with the direction of flow of the medium.

The illustration of FIG. 3 also shows clearly that during the production of the measurement path 3 of the housing part 5 it is essentially sufficient to contact two identically shaped spike-like slide feed in the mold, with their contact line extending between the opposite ends 15 of the projecting areas 16 in the area of the openings of the measurement section 3.

Thus, the above-described invention relates to an ultrasonic measuring arrangement 1 for the flow, speed of sound, density, viscosity, and/or temperature measurement of flowing media, comprising a measurement tube 2 that has a measurement section 3, which is arranged in an area of the measurement housing 4, with the ultrasound measuring arrangement comprising a medium for sound transmission through the measurement section 3 in the direction of flow and opposite thereto and at least two ultrasound transceivers provided as sensors, arranged at a distance for collecting signals. In order to provide an ultrasonic measuring arrangement 1 that can be produced easily and cost-effectively, has a small nominal diameter, and allows a direct sound transmission through the measurement section 3 with a transmission power as low as possible, it is suggested that the measurement tube (2) of the arrangement (1) is embodied free from seals and seams and that the sensors are arranged in the end sections of the measurement tube (2) such that the sound path forms an acute angle with the direction of flow of the medium, which is not zero degrees.

The invention claimed is:

1. An ultrasonic measuring arrangement for at least one of flow, speed of sound, density, viscosity, or temperature of a flowing media, comprising a measurement tube with a measurement section, which is arranged in an area of a measurement housing, at least two ultrasonic transceivers as sensors, arranged spaced apart from one another, for sound transmission through the measurement section in a direction of flow of the medium and opposite thereto and for recording signals, the measurement tube (2) of the arrangement (1) is embodied without any seams and seals and is embodied in one piece with a housing part (5) without any seams or seals, and the sensors are arranged in end sections of the measurement tube (2) such that a sound path between the sensors forms an acute angle with the direction of flow of the medium, which is not zero degrees.

2. An ultrasonic measuring arrangement according to claim 1, wherein the sound path is embodied without any reflections.

3. An ultrasonic measuring arrangement according to claim 1, wherein the sensors in the end sections of the measurement tube (2) are arranged such that they do not contact the medium.

4. An ultrasonic measuring arrangement according to claim 1, wherein a cross-section of the sound path changes over a longitudinal extension of the measurement section (3) with an area the medium flows through essentially remaining the same.

5. An ultrasonic measuring arrangement according to claim 1, wherein the housing part (5) is provided with connections (6), which are arranged symmetrically with regards to a reflector level extending perpendicularly to the longitudinal extension of the housing part (5) in a middle of the housing.

6. An ultrasonic measuring arrangement according to claim 5, wherein an installation chamber is provided on the housing part (5), including an access opening (17) facing away from the measurement tube (2).

7. An ultrasonic measuring arrangement according to claim 5, wherein one or more additional housing parts are provided on the housing part (5).

8. An ultrasonic measuring arrangement according to claim 1, wherein the housing part (5), combined with another housing part, forms a structural chamber, in which a signal processing device is provided.

9. An ultrasonic measuring arrangement according to claim 8, wherein the housing part (5) or the housing parts are made from plastic.

10. An ultrasonic measuring arrangement according to claim 1, further comprising a fastening element (9) on the housing part (5) for fastening it.

* * * * *